(12) United States Patent
Koester (10) Patent No.: US 9,949,416 B2
(45) Date of Patent: Apr. 17, 2018

(54) PROTECTION FOR IMPLANTED GOLD SURFACES

(75) Inventor: Kurt J. Koester, Los Angeles, CA (US)

(73) Assignee: ADVANCED BIONICS AG, Staefa (CH)

( * ) Notice: Subject to any disclaimer, the term of this patent is extended or adjusted under 35 U.S.C. 154(b) by 1011 days.

(21) Appl. No.: 13/993,019

(22) PCT Filed: Dec. 14, 2011

(86) PCT No.: PCT/US2011/064853
§ 371 (c)(1),
(2), (4) Date: Aug. 19, 2013

(87) PCT Pub. No.: WO2012/082863
PCT Pub. Date: Jun. 21, 2012

(65) Prior Publication Data
US 2013/0319717 A1    Dec. 5, 2013

Related U.S. Application Data

(60) Provisional application No. 61/423,320, filed on Dec. 15, 2010.

(51) Int. Cl.
*H05K 13/00* (2006.01)
*H05K 5/06* (2006.01)
(Continued)

(52) U.S. Cl.
CPC .............. *H05K 13/00* (2013.01); *A61F 11/04* (2013.01); *A61N 1/3754* (2013.01); *B05D 1/185* (2013.01);
(Continued)

(58) Field of Classification Search
CPC ................... H05K 13/00; H05K 5/069; Y10T 428/31529; Y10T 428/31663; Y10T 428/31678
See application file for complete search history.

(56) References Cited

U.S. PATENT DOCUMENTS 4,497,890 A * 2/1985 Helbert ..................... G03F 7/11
257/E21.259
4,964,972 A * 10/1990 Sagiv ..................... B82Y 15/00
204/418

(Continued)

FOREIGN PATENT DOCUMENTS

| EP | 2123269 | 11/2009 |
| WO | 2010017816 A1 | 2/2010 |
| WO | 2010025517 A1 | 3/2010 |

OTHER PUBLICATIONS

"Pot", Retrieved Jun. 16, 2016 from http://www.merriam-webster.com/dictionary/pot.*

(Continued)

*Primary Examiner* — Nicole Buie-Hatcher
(74) *Attorney, Agent, or Firm* — Fabian VanCott; Steven L. Nichols (57) ABSTRACT

An implantable device includes an exterior gold surface and a thin film disposed on the exterior gold surface and forming a barrier between the exterior gold surface and an implanted environment, in which the thin film includes molecules with a head portion, the head portion attached to the exterior gold surface.

9 Claims, 5 Drawing Sheets

(51) Int. Cl.
 A61F 11/04 (2006.01)
 B05D 1/18 (2006.01)
 B82Y 30/00 (2011.01)
 B82Y 40/00 (2011.01)
 A61N 1/375 (2006.01)
(52) U.S. Cl.
 CPC ............... *B82Y 30/00* (2013.01); *B82Y 40/00* (2013.01); *H05K 5/069* (2013.01); *B05D 2258/00* (2013.01); *Y10T 428/31529* (2015.04); *Y10T 428/31663* (2015.04); *Y10T 428/31678* (2015.04)

(56) References Cited

U.S. PATENT DOCUMENTS

| | | | | |
|---|---|---|---|---|
| 5,204,143 | A * | 4/1993 | Nishimiya | B41N 3/038 427/387 |
| 5,830,539 | A | 11/1998 | Yan et al. | |
| 6,252,307 | B1 | 6/2001 | Appelt | |
| 6,284,391 | B1 * | 9/2001 | Crook | C09D 183/08 428/420 |
| 6,500,108 | B1 | 12/2002 | Sorensen et al. | |
| 6,505,077 | B1 * | 1/2003 | Kast | A61N 1/08 607/61 |
| 6,583,251 | B1 | 6/2003 | Chaikof | |
| 7,524,535 | B2 | 4/2009 | Kim et al. | |
| 8,277,227 | B2 | 10/2012 | Darley et al. | |
| 8,323,333 | B2 | 12/2012 | Furst | |
| 8,538,530 | B1 * | 9/2013 | Orinski | A61N 1/3754 607/36 |
| 8,552,311 | B2 | 10/2013 | Koester | |
| 2002/0102405 | A1 * | 8/2002 | Chapman | A61L 15/42 428/411.1 |
| 2005/0002856 | A1 | 1/2005 | Klaveness | |
| 2005/0233158 | A1 | 10/2005 | Tour et al. | |
| 2006/0057180 | A1 * | 3/2006 | Chilkoti | A61L 27/34 424/422 |
| 2007/0054127 | A1 * | 3/2007 | Hergenrother | A61L 27/18 428/411.1 |
| 2007/0123766 | A1 | 5/2007 | Whalen, III et al. | |
| 2007/0239268 | A1 * | 10/2007 | Fox | A61L 27/306 623/1.46 |
| 2008/0152929 | A1 * | 6/2008 | Zhao | A61L 31/10 428/447 |
| 2009/0243756 | A1 * | 10/2009 | Stevenson | H01G 4/40 333/172 |
| 2010/0241071 | A1 | 9/2010 | Atanasoska | |
| 2010/0256747 | A1 * | 10/2010 | Hausbeck | A61L 31/022 623/1.46 |
| 2011/0004148 | A1 * | 1/2011 | Ishii | A61F 2/958 604/20 |
| 2011/0257702 | A1 | 10/2011 | Kara et al. | |
| 2012/0012374 | A1 | 1/2012 | Koester | |
| 2012/0016444 | A1 * | 1/2012 | Koester | A61N 1/3754 607/57 |
| 2012/0021200 | A1 * | 1/2012 | Koberstein | C08G 77/045 428/220 |
| 2012/0226001 | A1 * | 9/2012 | Brook | C07F 7/0852 525/477 |

OTHER PUBLICATIONS

Barbosa, "Inflammatory Responses to Biomaterials: Interaction between Leukocytes and Self-Assembled Monolayers," PhD Thesis, 2005.
Hou et al., "Inhibition of *Escherichia coli* Biofilm Formation by Self-Assembled Monolayers of Functional Alkanethiols on Gold," Applied and Environmental Microbioilogy, Jul. 2007, vol. 73, No. 13, 4300-4307.
Sabatani and Israel Rubinstein, "Organized self-assembling monolayers on electrodes. 2. Monolayer-based ultramicroelectrodes for the study of very rapid electrode kinetics," J. Phys. Chem., Dec. 1987, 91, 6663-6669.
Self-Assembled Monolayers, IBM Corporation, 1995. Downloaded Aug. 9, 2010 from http://zurich.ibm.com/~bmi/sam.html.
Tam-Chang and I. Iverson, Applications of Self-Assembled Monolayers (SAMs) of Alkanethiolates on Gold, Adsorption and its Applications in Industry and Environmental Protection Studies in Surface Science and Catalysis, vol. 120 917, A Dabrowski (Ed.), Elsevier Science B.V., 1998.
Tlili et al., "Electrical Characterization of a Thiol SAM on Gold as a First Step for the Fabrication of Immunosensors based on a Quartz Crystal Microbalance," Sensors, Aug. 30, 2004, 4, 105-114.
Yokoyama et al., "Electron Tunneling through Pseudomonas aeruginosa Azurins on SAM Gold Electrodes," NIH Public Access Author Manuscript, Mar. 3, 2008, 361(4): 1095-1099.
Zamborini et al., "Corrosion Passivation of Gold by n-Alkanethiol Self-Assembled Monolayers: Effect of Chain Length and End Group," Langmuir, May 13, 1998, 14(12), pp. 3279-3286.

* cited by examiner

PROTECTION FOR IMPLANTED GOLD SURFACES

RELATED DOCUMENTS

The present application claims the benefit under 35 U.S.C. § 371 to International PCT application No.: PCT/US2011/064853 filed Dec. 14, 2011 which claims the benefit under 35 U.S.C. § 119(e) of U.S. Provisional Application No. 61/423,320, entitled "Protection for Implanted Gold Surfaces" filed Dec. 15, 2010, which applications are incorporated herein by reference in their entirety.

BACKGROUND

Hermetically sealed cases can be used to isolate electronic devices from environmental contamination. To form electrical connections between the interior and the exterior of a hermetically sealed case, a hermetic feedthrough can be used. This hermetic feedthrough maintains the integrity of the hermetic sealed case, while allowing electrical signals to pass through. The sealed case and hermetic feedthrough may have a number of gold surfaces. For example, gold braze joints can be used to seal electrically conductive pins into the feedthrough or to seal the feedthrough into an aperture in the hermetic case. Gold is a relatively inert element and resists many types of chemical corrosion. However, in implanted environments gold can corrode, particularly when subjected to high electrical current densities.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Human implant technologies often make use of hermetically sealed devices. The hermetically sealed devices are substantially impermeable to liquids and gasses and prevent body fluids from damaging electronic components contained within the device. In an implanted environment, the hermetically sealed case is subject to a variety of corrosive chemicals and mechanical forces. However, the implanted case must be highly reliable over the lifetime of the biomedical device.

As mentioned above, a feedthrough is often used to form an electrical or physical connection between the interior and the exterior of a sealed case. An electrical feedthrough maintains the integrity of the hermetically sealed case, while allowing electrical signals to pass through. The electrical feedthrough is often constructed as a separate element and then sealed into an aperture in a wall of the case. A variety of gold elements can be incorporated into the hermitically sealed device and feedthrough. For example, gold elements can be incorporated as pins, coatings, joints, or other components. For example, it can be desirable to use a gold brazing process as a means of joining components of the feedthrough and/or joining the electrical feedthrough to the implant housing. Gold brazing is a well understood process that is used in a large number of active biomedical implants. Further, gold is a relatively inert element and resists many types of chemical corrosion. However, some implant devices, such as cochlear implants, pass relatively high currents through and around the gold joints. As current densities increase, the susceptibility of the gold joint to chemical corrosion also increases. Where a gold joint is used to seal conductive pins into an electrical feedthrough, the gold joint is part of the current path. Where a gold joint is used to seal the electrical feedthrough to the case, the gold joint may be part of the grounding path for the device. The resulting current densities and voltage potentials may lead to increased surface corrosion of the gold.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

As used in the specification and appended claims, the term "pin" refers to an electrically conductive channel between the exterior and interior of a hermetic feedthrough. A pin may have a wide variety of shapes including circular, square, rectangular, elliptical, irregular, or other shapes. Further, in some examples such as co-axial feedthroughs, pins may be nested within other pins. As used in the specification and appended claims, the term "thin film" is used broadly to refer to films ranging from fractions of a nanometer (a monolayer) to microns in thickness.

Figure 1:
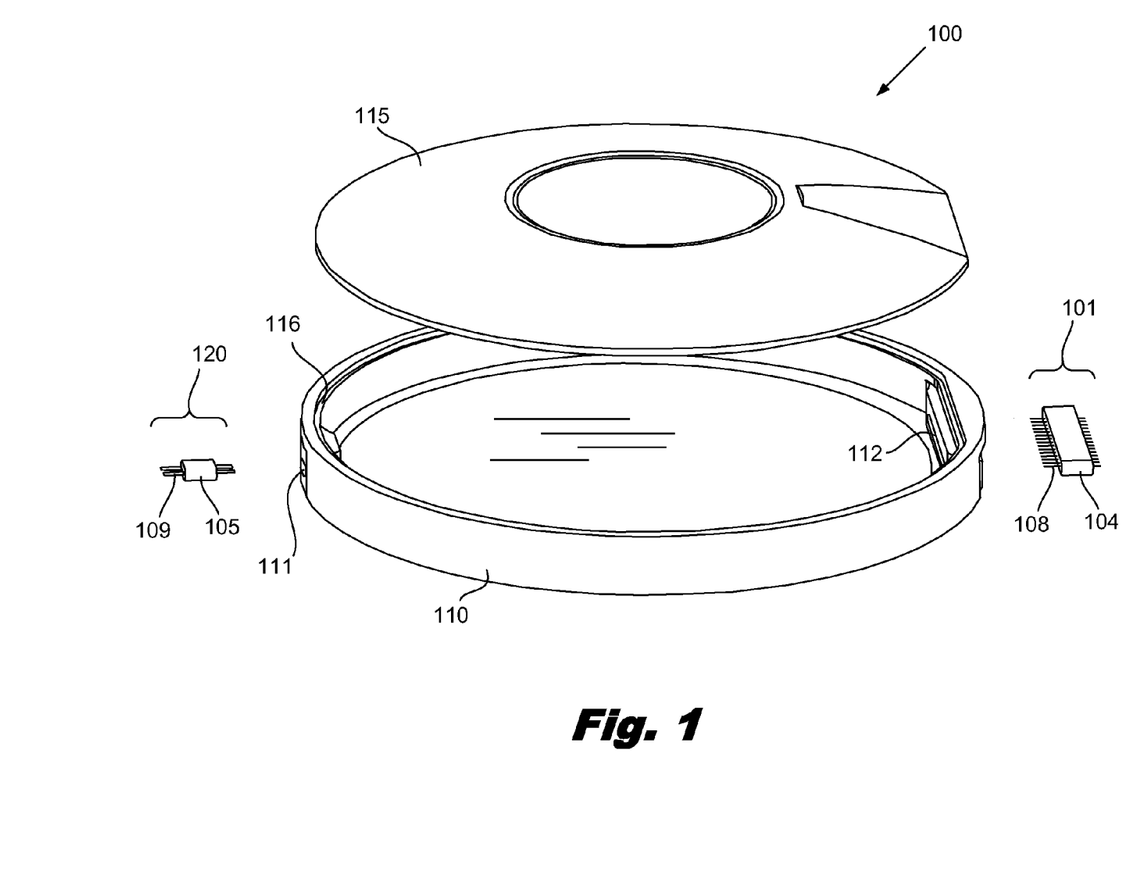
FIG. 1 is an exploded view of an illustrative hermetically sealed case, according to one example of principles described herein.

FIG. 1 is an exploded view of an illustrative hermetic enclosure (100) that houses cochlear implant electronics. In this particular example, the hermetic enclosure (100) includes a case (110) and a case top (115). The case (110) and the case top (115) may be formed from a variety of biocompatible materials. For example, the case (110) and case top (115) may be formed from metals, ceramics, crystalline structures, composites, or other suitable materials. The outer case (110) may be formed from a single piece of material or may include multiple pieces. The multiple pieces may be connected using a variety of techniques including, but not limited to, brazing, laser welding, or bonding.

Figure 4A:
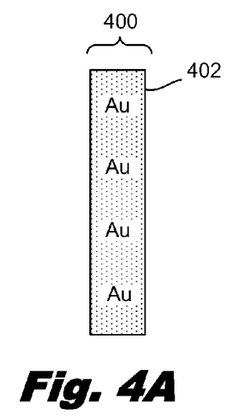
FIGS. 4A-4E are diagrams showing illustrative surface treatments for protecting implanted gold surfaces, according to one example of principles described herein.

According to one illustrative example, the case (110) and the case top (115) are formed from titanium. The case (110) shown in FIG. 4A is a closed-bottom cylinder that is machined, stamped, or otherwise formed from a single piece of titanium. In this example, the case (110) includes two apertures (111, 112) that are configured to receive hermetic electrical feedthroughs (101, 120). The case top (115) is also made from titanium and can be placed onto a ledge (116) machined into the upper rim of the case (110). The case top (115) can then be laser welded or brazed onto the case (110). Once the case top (115) and hermetic electrical feedthroughs (101, 120) are in place, the hermetic enclosure (100) prevents liquids or gasses from entering the interior of the enclosure (100). As discussed above, this prevents damage to electronics or other components housed in the interior of the hermetic enclosure (100).

The electrical feedthroughs (101, 120) may be formed from a variety of materials and have a number of different configurations. According to one illustrative example, the electrical feedthroughs (101, 120) include a set of conductors (108, 109) that are imbedded in ceramic bodies (104, 105). The conductors (108, 109) pass through and are sealed in the ceramic body. The sealing of the conductors to the ceramic body may take place in a variety of ways, including gold brazing or partially transient liquid phase (pTLP) bonding.

The ceramic body (104, 105) is then joined to the appropriate aperture (111, 112) in the case (110). A variety of techniques, including gold braze joints can be used to join the ceramic body to the case (110). In this illustrative example, the hermetic feedthroughs (101, 120) are on the perimeter of the case (110). The hermetic feedthroughs (101, 120) are well protected by the case (110) to minimize damage from impact loads. Although the feedthroughs (101, 120) are illustrated as being located in the perimeter of the case (110) in this example, the feedthroughs could also be located at other sites on the case (110) or the case top (115). Further, the number and size of hermetic feedthroughs (101,120) could be varied according to the design requirements. For example, a single feedthrough could be used to access all electrical connections to the internal electronics.

Figure 2A:
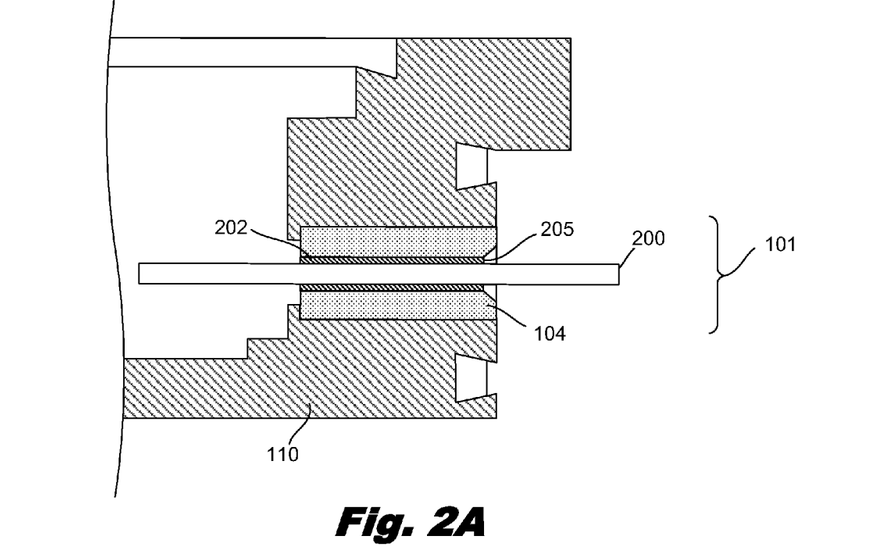
FIG. 2A is a cross-sectional view of an illustrative electrical feedthrough that includes conductive pins that are hermetically sealed into a ceramic body using a gold braze joint, according to one example of principles described herein.
Figure 2B:
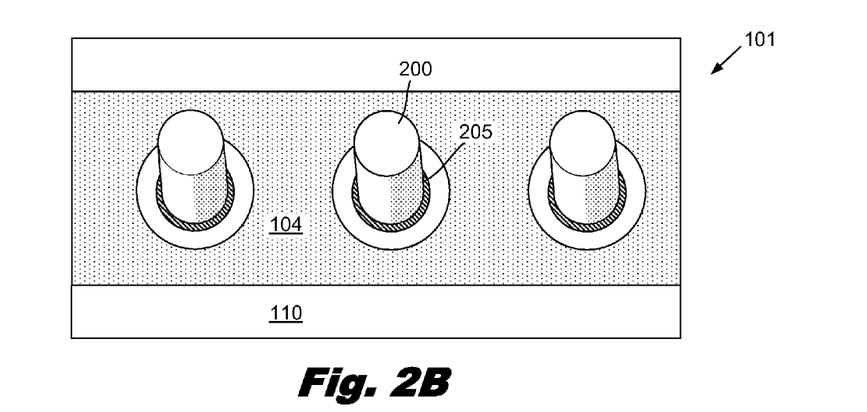
FIG. 2B is a perspective view of the illustrative electrical feedthrough shown in FIG. 2A, according to one example of principles described herein.

FIGS. 2A and 2B illustrate a feedthrough (101) that includes cylindrical pins (200) that are sealed into the ceramic body (104) using a gold braze joint (202). FIG. 2A is a cross-sectional view of a portion of the case (110) that includes the feedthrough (101). The left side of the pin (200) is connected to components that are internal to the case (110) and the right side of the pin (200) is connected to components that are external to the case (110). As discussed above, the pin may have a variety of geometries and may be formed from a variety of materials. In this example, the pins (200) are cylindrical and may be formed from platinum or a platinum alloy such as platinum iridium. The right hand surface (205) of the gold braze joint (202) is on the external side of the hermetic case (100, FIG. 1) and can be corroded by exposure to bodily fluids.

FIG. 2B is a perspective view of a portion of the hermetic case (110) that includes part of the hermetic feedthrough (101). As discussed above, the ceramic body (104) surrounds the pins (200), which are sealed with a gold joint (202). As discussed above, the gold braze joint (202, FIG. 2A) in this example becomes part of the conductive pathway through the feedthrough (101). Consequently, a significant amount of electrical current may pass through the gold braze joint (202, FIG. 2A). Additionally, the gold braze joint (202, FIG. 2A) also may have an electrical voltage potential that is significantly different than the surrounding body tissues. As a result, the exterior surface (205) of the gold braze joint may have a tendency to corrode when in contact with body fluids and tissues.

The braze joint (202) may be formed in a variety of ways. For example, the gold braze joint (202) may be formed by placing the platinum pins through holes in a fully densified ceramic body (104). The platinum pins (200) and ceramic body (104) are heated, and melted gold or a gold alloy is drawn by capillary action into the gap between the platinum pin (200) and the ceramic body (104).

In an alternative example, two layers of green ceramic tape are used to form the ceramic body. The pins (200) are coated with a layer of gold around their circumference and laid on a bottom layer of green ceramic tape. An upper layer of green ceramic tape is laid over the pins (200) and the bottom layer. This sandwiches the gold coated pins (200) between two layers of ceramic tape. The green ceramic tape is then densified by the application of heat and pressure. The upper and lower ceramic layers are joined to form the ceramic body (104), and the gold forms a seal between the ceramic body (104) and the pins (200).

A variety of additional steps and alternative methods can be used to form the gold braze joint (202). For example, a number of cleaning steps may be employed to ensure a satisfactory bond between the gold, ceramic, and platinum. Flux and surface coatings could also be used. The gold could be alloyed with a number of other elements, including platinum, nickel, titanium, palladium, iridium, or copper. In some examples, the creation of the gold braze joint could incorporate principles used in active metal brazing or include filler material.

The ceramic body (102) can be joined to the case (110) in a number of ways, including brazing, active metal brazing, ceramic/glass/metal joining, transient liquid phase bonding, or other suitable techniques.

Figure 3A:
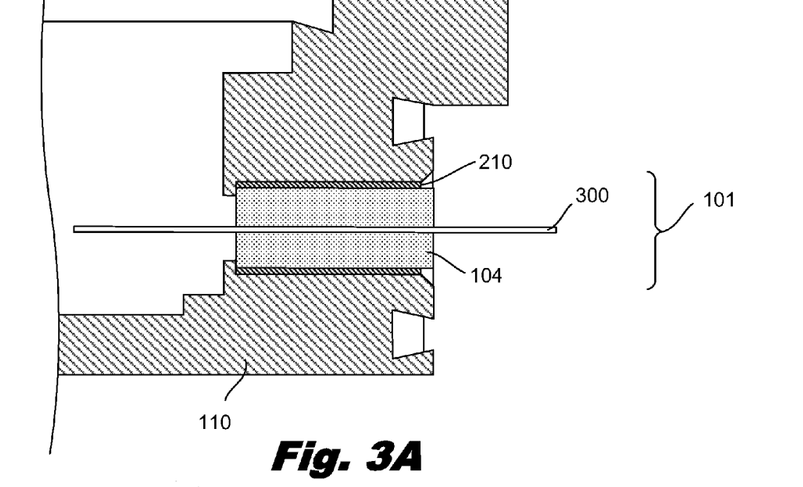
FIG. 3A is a cross-sectional view of an illustrative electrical feedthrough that is joined to a case using a gold braze joint, according to one example of principles described herein.
Figure 3B:
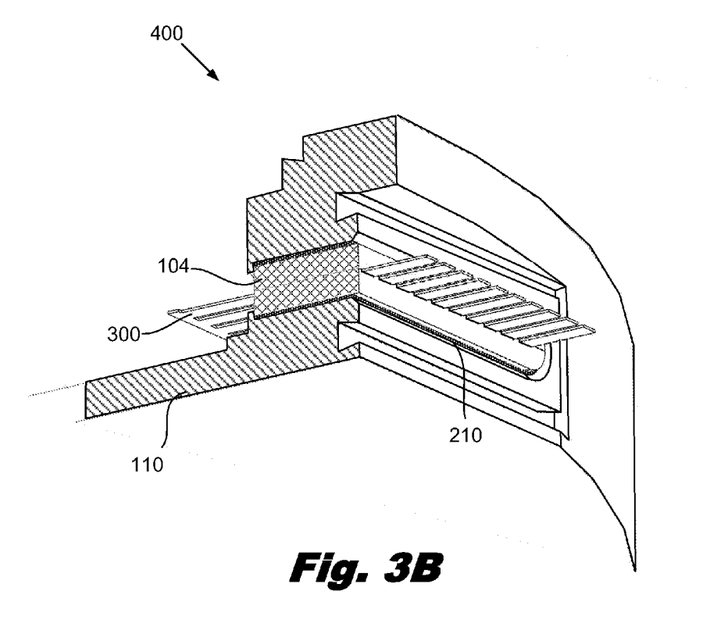
FIG. 3B is a cut-away perspective view of the illustrative electrical feedthrough shown in FIG. 3A, according to one example of principles described herein.

FIGS. 3A and 3B are diagrams of an illustrative feedthrough (101) that is joined to a case (110) using a gold braze joint (210). FIG. 3A is a cross-sectional diagram of the hermetic case (110) and feedthrough (101). This figure shows ribbon vias (300) passing through the ceramic body (104) and extending from both sides of the ceramic body (104). The braze joint (210) seals the ceramic body (104) to the case (110). As discussed above, the case (110) may be formed from any biocompatible material that has the desired impermeability and mechanical characteristics. For example, titanium may be used to form the case. Titanium has a number of desirable characteristics, including high strength, resiliency, biocompatibility, low density, and low permeability.

The ceramic body (104) may be formed from a variety of materials. For example, the ceramic body (104) may be formed from alumina. The ribbon vias (300) may also be formed from a range of materials that have the desired characteristics. For example, the ribbon vias (300) may be formed from platinum or platinum alloy. Platinum has a number of desirable characteristics, including a relatively low electrical resistance, high malleability, biocompatibility, and ability to be alloyed with a number of other elements. In other examples, the ribbon vias (300) may be gold plated or formed from gold or gold alloy.

In this illustrative example, the ribbon vias (300) could be sealed into the ceramic body (102) using partially transient liquid phase (pTLP) bonding. A number of methods and feedthroughs that use platinum ribbon vias sealed into a ceramic body using pTLP bonding are described in U.S. patent application Ser. No. 12/836,831 entitled "Electrical Feedthrough Assembly," to Kurt J. Koester, filed on Jul. 15, 2010, which is incorporated herein by reference in its entirety.

The gold braze joint (210) is electrically insulated from the ribbon vias (300) and consequently does not directly conduct electricity through the feedthrough. However, the titanium case (110) may form the ground plane for the device. Because the gold braze joint (210) is in direct electrical contact with the titanium case, the gold braze joint (210) is also subjected to the currents and voltages associated with the grounding of the device. As discussed above, the surface portions of the gold braze joint (210) that are on the exterior of the device are exposed to bodily fluids and may be susceptible to corrosion.

Illustrative examples of two gold braze joints used in an electrical feedthrough are given above. These are only illustrative examples and are not meant to be limiting. A variety of other gold elements could have exterior gold surfaces. For example, the conductive pins that pass through the ceramic may be formed from gold or may be gold coated. Wires, connectors, pads, ball bonds, or other elements could also be formed from gold and have exterior gold surfaces that may also benefit from the surface protection afforded by the thin film techniques described below. The techniques described below are not limited to implanted devices, but can be used in a variety of other applications as well. For example, gold braze joints can be used in aerospace, industrial, microfluidics, medical equipment, and other applications.

FIGS. 4A-4E show a number of illustrative surface treatments that can be used to protect an exterior gold surface (402) of an implanted device from the implanted environment. As discussed above, the exterior gold surface (402) may be any surface that is exposed to the implanted environment. For example, the exterior gold surface may be a surface of a braze joint, gold pin, gold plated platinum pin, tape automated bond, a ball bond, a weld joint, a surface plating, or other component of the hermetic device.

Figure 4B:
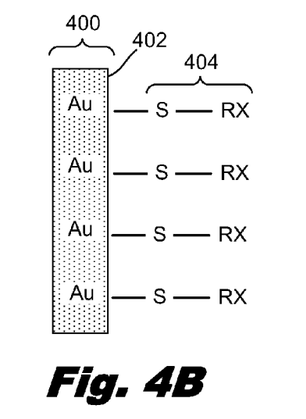

FIG. 4A shows a gold body (400) with a exterior gold surface (402). As shown by FIGS. 4B-4E, this surface (402) is prepared and treated with a thin film (404), FIG. 4B shows a thin film (404) that is composed of a number of molecules that are attached to the exterior gold surface (402). In this example, each molecule in the thin film (404) includes two functional groups: a first functional group that bonds to the gold surface and a second functional group that extends away from the gold surface. For example, the first functional group may include a sulfur molecule, designated the "S" in FIG. 4B. Sulfur and sulfur containing molecules may have a number of advantages, including forming strong bonds with gold and with a variety of other functional groups or organic molecules. The bond between sulfur and gold is relatively strong, with a bond energy of greater than 400 kJ/mol.

Examples of the thin film (404) include organosulfur compounds that contain a sulfur-hydrogen bond. A functional group "X" attaches to an appropriate chemical background illustrated by the thiol molecule "R". Reaction by-products are not shown. The functional group "X" can be selected to attach to a variety of molecules, including potting materials, silicone, silicon, or other molecules.

Figure 4C:
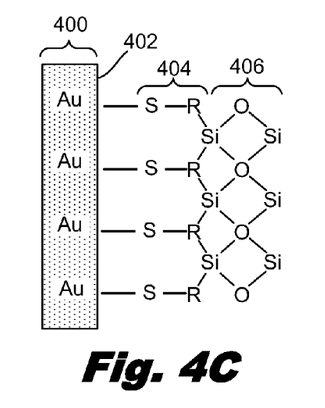

FIG. 4C shows the molecule "R" that is attached to a sol gel to form a glass (406). The glass (406) is shown as interconnected silicon and oxygen atoms. The glass is substantially impervious to chemical attack and protects the underlying gold surface (402) from corrosion by forming a barrier between the gold surface (402) and the implanted environment.

Figure 4D:
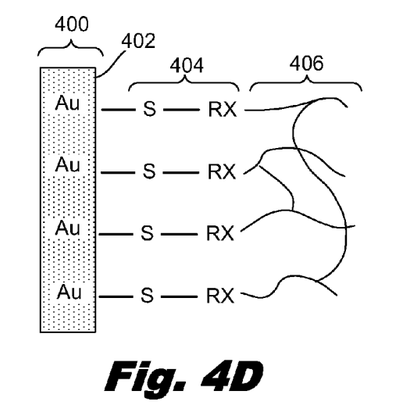

FIG. 4D shows an alternative example in which the functional group "X" is attached to a hydrophobic agent (406) that prevents fluids and water soluble chemicals from contacting the gold surface (402). For example, these hydrophobic molecules may include silicone. In other examples, the functional group may be an epoxide or polyamine that bonds to components within an epoxy potting agent. For example, the functional group may be a phenolic, aliphatic or polyamine molecule.

In this example, all molecules are identical; however, a variety of different molecules may be attached to the same gold surface to achieve the desired protection of the surfaces. Further, each molecule may terminate in more than one functional group that bonds with overlying material.

Figure 4E:
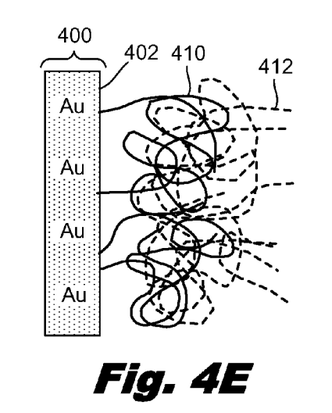

FIG. 4E shows an entanglement coupling agent (410) directly attached to the exterior gold surface (402). In this example, the entanglement coupling agent (410) is long chain that is functionalized on one end. This functionalized end attaches to the exterior gold surface (402). The tail portion of the entanglement coupling agent (410) then extends into the potting material and is entangled with molecules in the potting material. This provides for more secure attachment of a potting material (412). The potting material (412) may be a variety of materials including medical grade silicone. This strongly adhered potting material protects the exterior gold surface by creating a barrier between the gold surface and corrosive fluids or vapors in the implanted environment.

FIGS. 4A-4E are illustrative schematic representations of molecular configurations that could be used. The actual molecular configurations of these coatings may be less regular than illustrated in FIGS. 4A-4E. For example, FIG. 4C shows uniform and symmetrical attachments between molecules, which may or may not be realized in any given actual implementation.

Each of FIGS. 4C through 4E represents water impermeable barriers that prevent penetration of water for a long period of time. As used in the specification and appended claims, the term "water impermeable barrier" is used to describe barriers that prevent medically significant amounts of liquid water, water vapor, or aqueous solutions from penetrating the barrier in an implanted environment for a period of at least 30 days. For example, a water impermeable barrier may prevent substantial contact between aqueous solutions present in the implanted environment from contacting the underlying gold surface for a period of one year or longer.

Figure 5:
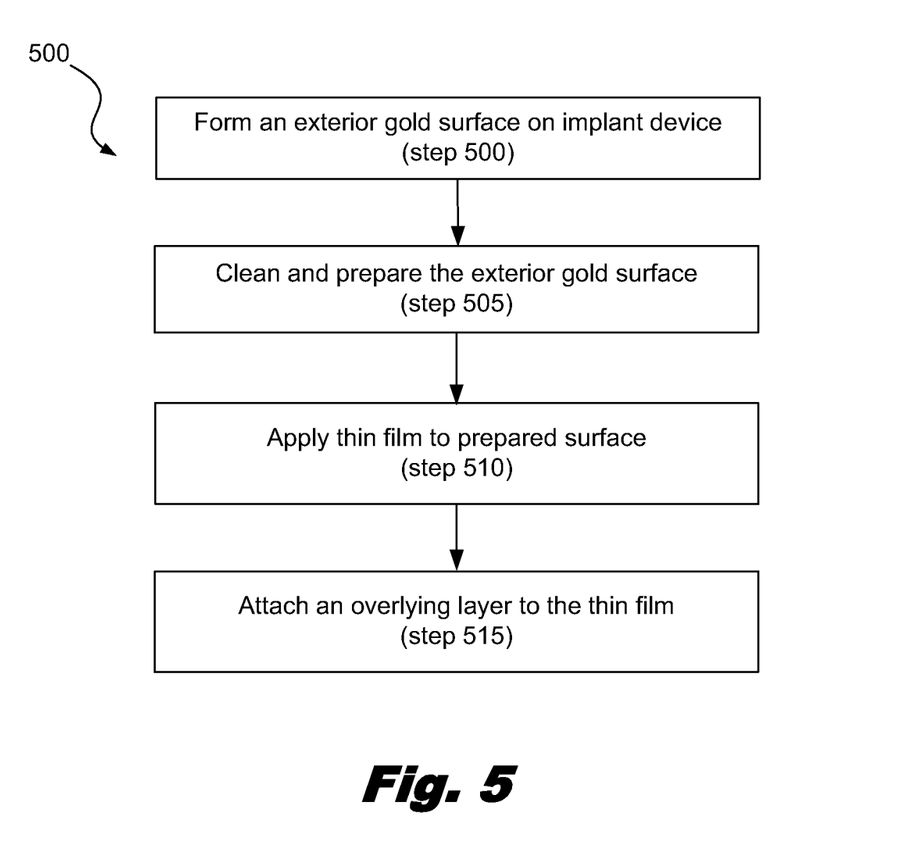
FIG. 5 is a flowchart showing an illustrative method for creating surface treatments for protecting implanted gold braze joints, according to one example of principles described herein.

FIG. 5 is an illustrative method for surface modification of exterior gold surfaces of implantable devices. The exterior gold surface is formed on the implanted device (step 500). As discussed above, the exterior gold surface may be a coating, joint, pin, wire, or other component of the implanted device. For example, the exterior gold surface can be a gold braze joint that acts as a structural seal between the feedthrough body and an aperture or a structural seal between a hermetic feedthrough body and conductive pins. The exterior gold surface is then cleaned and prepared (step 505). For example, various etching solutions and/or mechanical abrasion may be used to remove any contaminates from the surface of gold braze joint. The thin film is applied to the prepared surface (step 510). As discussed above, the thin film molecules may have a head portion that has an affinity for the gold surface and a tail portion that terminates in a functional group.

In one example, the thin film may be a self assembled monolayer (SAM). The SAM is created by the chemisorption of the head portions onto the gold surface from either a vapor or liquid. The tail portions, which include a coupling agent, are then organized. The SAM molecules are brought into contact with the gold surface and become closely assembled in an orderly monolayer array. In some examples, the SAMs may be an alkanethiol. For example, the head portion designed to attach to a gold surface may be an organosulfur. The sulfur has a strong affinity for the gold surface.

The coupling agent in the tail portion may be a long entangling molecule or a functionalized molecule. For example, the tail may be made of an alkyl chain with a terminal end that is functionalized. This functionalization may be achieved by adding —OH, —NH$_3$, —COOH, or other groups at the terminal end of the tail. The functional groups can be selected to achieve the desired wetting and interfacial properties.

A overlying layer is attached to thin film (step 515). In one implementation, the overlying layer may be formed from protective molecules attached to the functional group of the thin film molecules. As discussed above, the protective molecules may be any of a number of molecules, including sol gels, molecules that alter the hydrophobic and/or lipophobic character of the surface, molecules that prevent fluid and vapor contact with the gold surface, entanglement molecules that interlock with potting materials, or other suitable molecules that protect the gold surface from corrosion. In some examples, a combination of protective molecules with different types may be combined to provide increased surface protection.

In sum, gold surfaces may be protected from corrosion in a chemically active environment using a thin film coating. The properties of these thin film coatings can be tuned to create a glass layer, entangle potting material, adjust the wetting characteristics of the gold, create a barrier that prevents fluid and vapor contact with the exterior gold surface, and produce other desirable surface modifications.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An implantable device comprising:
    a gold body with an exterior gold surface, wherein the gold body is a braze joint that forms a hermetic seal between a first element and a second element of the implant device, wherein the first element comprises a ceramic feedthrough and the second element comprises a titanium housing; and
    a thin film disposed on the exterior gold surface,
    in which the thin film comprises molecules each of which includes two functional groups located, respectively, at a head portion and a tail portion of the molecule, the functional group of the head portion attached to the exterior gold surface and the functional group of the tail portion attached to an overlying layer of protective molecules that forms a water impermeable barrier and the overlying layer of protective molecules comprises an epoxy and the tail portion of the molecules comprise an epoxide or polyamine bonded with the epoxy.

2. The device of claim 1, wherein the head portion comprises a sulfur atom.

3. The device of claim 1, wherein the overlying layer of protective molecules forms a water impermeable barrier between the exterior gold surface and an implanted environment.

4. The device of claim 1, wherein the thin film comprises a self assembled monolayer.

5. The device of claim 4, wherein the thin film comprises alkanethiol.

6. The device of claim 1, wherein the gold braze joint is electrically connected to the titanium housing, the titanium housing serving as a ground plane for the device.

7. A method for making a protected gold surface of the implantable device of claim 1, comprising:
    providing molecules having first and second ends;
    attaching the first ends of the molecules to the exterior gold surface to form the thin film; and
    subsequently attaching an overlying layer to the second ends of the molecules, wherein the overlying layer forms a water impermeable barrier and the second ends of the molecules comprises a functional group selected from the group consisting of: an epoxide and a polyamine.

8. An implantable device comprising:
    a gold body with an exterior gold surface, wherein the gold body is a braze joint that forms a hermetic seal between a first element and a second element of the implant device, wherein the first element comprises a ceramic feedthrough and the second element comprises a conductive pin passing through the ceramic feedthrough; and
    a thin film disposed on the exterior gold surface,
    in which the thin film comprises molecules each of which includes two functional groups located, respectively, at a head portion and a tail portion of the molecule, the functional group of the head portion attached to the exterior gold surface and the functional group of the tail portion attached to an overlying layer of protective molecules that forms a water impermeable barrier and the functional group of the tail portion comprises an entanglement coupling agent entangled with the overlying layer.

9. The device of claim 8, wherein the gold braze joint comprises part of the conductive path of the pin.

\* \* \* \* \*